(12) United States Patent
Glaug et al.

(10) Patent No.: US 6,565,548 B1
(45) Date of Patent: May 20, 2003

(54) INCONTINENT SHIELD FOR MALES

(75) Inventors: Frank S. Glaug, Chester Springs, PA (US); Jean A. Serafino, Clifton Heights, PA (US)

(73) Assignee: Tyco Healthcare Retail Services AG (CH)

( * ) Notice: Subject to any disclaimer, the term of this patent is extended or adjusted under 35 U.S.C. 154(b) by 0 days.

(21) Appl. No.: 09/477,904

(22) Filed: Jan. 5, 2000

(51) Int. Cl.[7] ................................................ A61F 13/15
(52) U.S. Cl. ........................ 604/385.03; 604/385.14; 604/387; 604/389; 604/391; 604/349
(58) Field of Search ................. 604/385.03, 385.09, 604/385.05, 385.14, 387, 389–391, 347, 349, 385.01; 2/403–405

(56) References Cited

U.S. PATENT DOCUMENTS

| | | | | |
|---|---|---|---|---|
| 3,559,648 A | * | 2/1971 | Mason .......................... 128/287 |
| 3,747,602 A |   | 7/1973 | Howard |
| 3,768,479 A |   | 10/1973 | Widlund |
| 4,505,707 A | * | 3/1985 | Feeney .......................... 604/393 |
| 4,555,245 A | * | 11/1985 | Armbruster .................. 604/396 |
| 4,597,759 A |   | 7/1986 | Johnson |
| 4,886,509 A | * | 12/1989 | Mattsson ...................... 604/349 |
| 4,964,860 A | * | 10/1990 | Gipson et al. ................ 604/391 |
| 4,995,873 A | * | 2/1991 | Knight ........................... 604/391 |
| 5,261,901 A | * | 11/1993 | Guay ............................. 604/391 |
| 5,290,270 A |   | 3/1994 | Fisher |
| 5,414,870 A | * | 5/1995 | Moretz et al. ................... 2/400 |
| 5,439,458 A |   | 8/1995 | Noel |
| 5,520,673 A |   | 5/1996 | Yarbrough et al. |
| 5,735,837 A | * | 4/1998 | Ishikawa .................... 604/385.1 |
| 5,810,799 A | * | 9/1998 | Slater ........................ 604/385.1 |
| 5,817,086 A |   | 10/1998 | Kling |
| 5,876,390 A |   | 3/1999 | Hall et al. |
| 5,947,948 A |   | 9/1999 | Roe et al. |
| 5,984,910 A | * | 11/1999 | Berke .......................... 604/352 |
| 6,105,174 A | * | 8/2000 | Nygren et al. ................. 2/403 |
| 6,129,718 A | * | 10/2000 | Wada ........................... 604/378 |
| 6,197,011 B1 | * | 3/2001 | Freitas et al. .......... 604/385.03 |

FOREIGN PATENT DOCUMENTS

| | | |
|---|---|---|
| DE | 9110045.3 | 11/1991 |
| DE | 29600384 | 4/1996 |
| DE | 29602160 | 4/1996 |
| EP | 0966933 | 12/1999 |
| FR | 2701389 | 8/1994 |
| GB | 2319187 | 5/1998 |

* cited by examiner

*Primary Examiner*—Weilun Lo
*Assistant Examiner*—Michael G. Bogart
(74) *Attorney, Agent, or Firm*—Caesar, Rivise, Bernstein, Cohen & Pokotilow, Ltd.

(57) ABSTRACT

A disposable absorbent shield for men which arranged to be worn in an undergarment to trap and collect small amounts of leaking urine. The shield has a flexible chassis and a pair of side-by-side adhesive stripes on it to releasably mount it within the undergarment. The adhesive stripes are initially covered by a removable release strip until the shield is ready for use. The chassis includes a front portion arranged to be located over the penis and contiguous lower abdominal region and a crotch portion arranged to be located in the crotch and between the legs. The chassis is made up of an outer cover, an inner liner and a liquid absorbent core interposed therebetween. The chassis is a very thin planar flexible structure having a modified T-shaped periphery including an upper transverse portion forming the upper portion of the chassis and a downwardly extending longitudinal portion forming the crotch portion of the chassis. The upper portion merges with the crotch portion in a pair of gently curved sides which are shaped to readily accommodate the legs of the wearer. The chassis is arranged to be readily bent into a desired shape to fit within the undergarment and to conform to the body of the wearer.

16 Claims, 2 Drawing Sheets

INCONTINENT SHIELD FOR MALES

FIELD OF THE INVENTION

This invention relates generally to disposable absorbent articles for males exhibiting minor incontinency, and more specifically to disposable absorbent shields which can be readily worn and concealed under clothing to prevent the soiling of such clothing by minor urine leakage.

BACKGROUND OF THE INVENTION

As populations continue to increase in longevity, incontinence, a problem of age presents a need for fluid control in undergarments. In particular, adult incontinence represents a transition from underwear to the use of some type of absorbent article to be added to the underwear or to completely replace it. For moderate-to-heavy incontinence needs a variety of disposable diaper designs are commercially available. Never the less certain deficiencies have been recognized in diapers that are currently found in the market place. For example, many of them, particularly high capacity designs, are thick and bulky, thus rendering concealment difficult. Moreover many of such prior art absorbent articles are complex in construction. See for example, U.S. Pat. No. 5,520,673 (Yarbrough et al.), U.S. Pat. No. 5,876,390 (Hall et al.), U.S. Pat. No. 5,817,086 (Kling), and U.S. Pat. No. 5,947,848 (Roe et al.), all of which disclose absorbent articles which may be of various shapes, such as rectangular, trapezoidal, T-shaped, I-shaped, hour-glass shaped, but which include various elastic components and/or other structural features, such as adhesive mounting tabs. Not all prior art diapers are of such complex construction. See for example, U.S. Pat. No. 3,768,479 (Widlund). This patent discloses a disposable diaper which is T-shaped, whose transverse or wider upper portion is made thicker and includes an elastic insert for stability. Since the diaper will be used on infants concealability of the diaper is not a significant concern, as is the case with incontinence shields to be worn within undergarments by adults. Moreover, the simple T-shape of the diaper leaves much to be desired from the standpoint of conformability to the wearer's body.

For light-to-moderate incontinence needs, absorbent pads, guards, shields or absorbent inserts which are used in conjunction with underwear have proven generally acceptable. Nevertheless, such prior art pads, guards, shields and absorbent inserts still leave much to be desired from the standpoint of concealability, comfort, cost, etc., for light or very minor incontinence (slight dripping or leakage).

OBJECTS OF THE INVENTION

Accordingly, it is a general object of this invention to provide a disposable absorbent shield which addresses the needs of the prior art.

It is another object of this invention to provide a disposable adult incontinent shield which is very thin and flexible to be readily worn and concealed under clothing.

It is still another object of this invention to provide a soft and flexible disposable incontinent shield.

SUMMARY OF THE INVENTION

A disposable absorbent shield arranged to be worn under clothing by a male person to trap and collect urine. The article is in the form of a flexible chassis having a front portion arranged to be located, over the person's penis and contiguous, lower abdominal region and a crotch portion arranged to be located over the person's crotch and between the person's legs. The chassis includes a liquid absorbent layer or core (e.g., an air-laid absorbent material containing super absorbent powder, pulp and a binder), an outer cover or moisture barrier (e.g., a polymeric film), and an inner liner (e.g., a non-woven cover-stock, such as spun bonded polypropylene). The liquid absorbent core is interposed between the outer cover and the inner liner.

The chassis is a very thin (e.g., in the range of 0.2 mm–6 mm and most preferably 1.0 mm thick), planar structure having a modified T-shaped periphery including an upper transverse portion (e.g., approximately 152 mm wide), forming the upper portion of the chassis and a downwardly extending longitudinal portion (e.g., approximately 245 mm long), forming the crotch portion of the chassis. The upper portion merges with the crotch portion in a pair of gently curved sides (e.g., radius of curvature approximately 78 mm), shaped to readily accommodate the legs of the wearer. The chassis is arranged to be bent into a desired shape to conform to the body of the wearer.

In accordance with one preferred embodiment of the invention the shield includes an adhesive (e.g., two lines or stripes of pressure sensitive hot melt adhesive) located on the outer cover (e.g., along the central axis of the shield) for releasably mounting the shield in an undergarment. The adhesive stripes are initially covered by a removable release strip until the shield is ready for use, e.g., affixation to the inside of the undergarment so that the shield will block the egress of urine through the undergarment.

DETAILED DESCRIPTION OF THE PREFERRED EMBODIMENT

Figure 1:
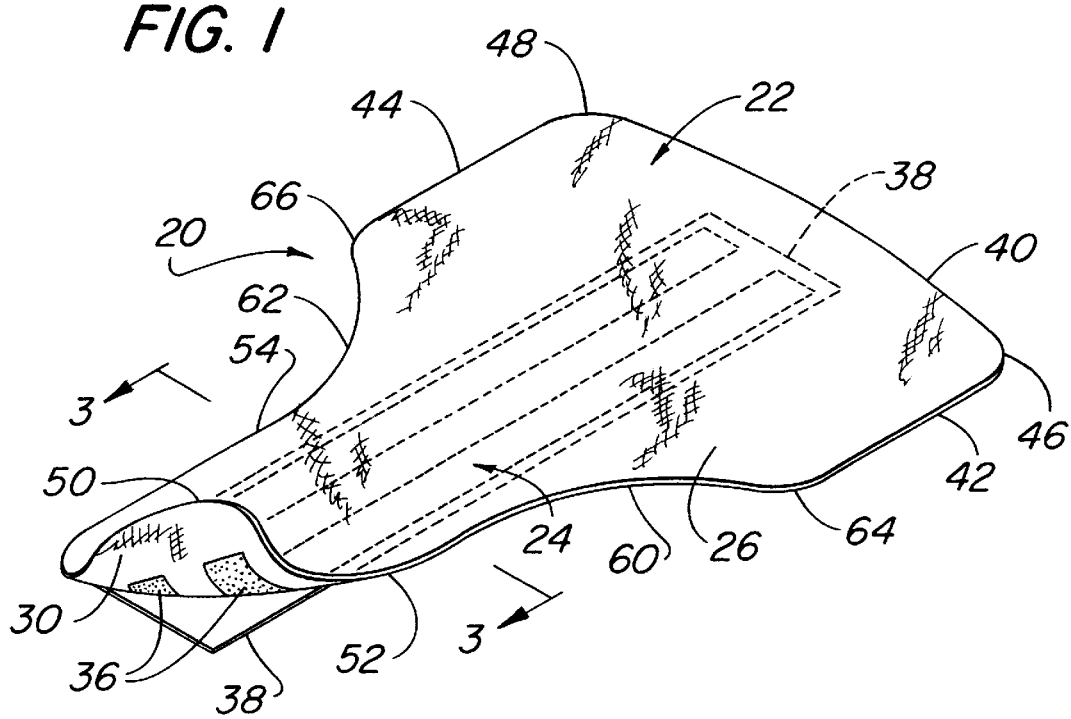
FIG. 1 is an isometric view of a shield constructed in accordance with this invention.

Referring now to the various figures of the drawing wherein like reference characters refer to like parts, there is shown in FIG. 1 a disposable absorbent article 20 constructed in accordance with one embodiment of this invention. The article 20 of FIG. 1 is in the form of an adult incontinent shield. The shield 20 basically comprises a chassis made up of an upper or front portion 22 and a lower crotch portion 24. The details of both portions will be described later. Suffice it for now to state that the shield is arranged to be mounted within an undergarment (not shown) so that the front portion 22 is located over the wearer's penis and contiguous lower abdominal region, while the crotch portion 24 is located at the crotch and between the wearer's legs.

Figure 3:
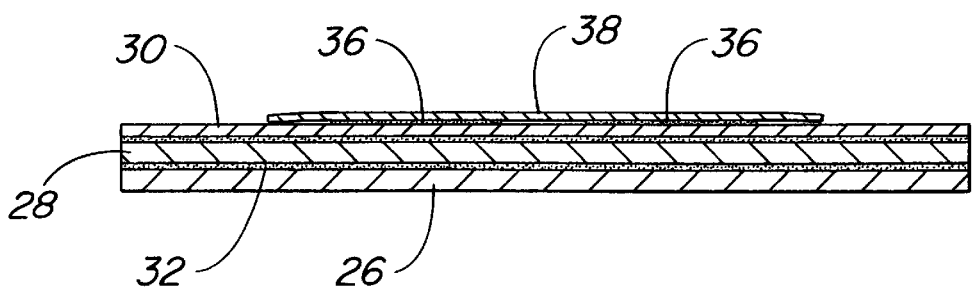
FIG. 3 is an enlarged sectional view taken along line 3—3 of FIG. 1.

As best seen in FIG. 3, the chassis is a very thin generally planar structure. In particular, the chassis may be any thickness in the range of 0.2 mm to 6 mm, with 1.0 mm being the most preferred thickness for the exemplary embodiment which will be described hereinafter. The chassis is formed of a liquid pervious inner liner or layer 26, a liquid absorbent, e.g., air-laid composite, core 28, and an outer cover or moisture barrier 30. The inner layer may be of any liquid pervious material. One particularly suitable material is a 17 gsm wettable nonwoven coverstock, made of thermal bond polypropylene, available from PGI Nonwovens, Landisville, N.J. The inner layer 26 is attached directly on-top of the absorbent core 28 by a low add-on adhesive 32. One particularly suitable material for the adhesive 32 is available from National Starch and Chemical of Bridgewater, N.J. under the trade designation #34-5637. The inner layer 26 may be formed of other material fibers (e.g., polyethylene, bi-component, polyester, rayon, cotton, etc.), fiber combinations (e.g., spunbond, air laid, wet laid, hydroentangled, etc.), and basis weights may be used as well. In fact, if desired, the inner layer 26 may be formed of a liquid impermeable material, e.g., polymeric film, having plural apertures or pores extending therethrough so as to make the material liquid permeable.

The outer layer or moisture barrier 30 is attached directly on-top of the absorbent core 28 on the opposite side from the inner layer 26 by a high add-on adhesive 34. One particularly suitable material for the adhesive 34 is the same as for adhesive 32.

The core 28 can be made up of any suitable absorbent material, as well as combinations of different types of absorbent material(s). For example, in the preferred embodiment shown herein the absorbent core 28 is a composite formed of an air-laid absorbent material containing super absorbent polymer powder (SAP), wood pulp and a binder. Examples of SAP include polyacrylamides, polyvinyl alcohol, polyacrylates, various grafted starches, and the like. One particularly suitable super absorbent material is a cross-linked polysodium acrylate, which can be purchased from Chemdal Corporation, Palatine, Ill., under the trademark ASAP 2260.

In order to hold the shield in place within the wearer's undergarment, the shield includes a pair of side-by-side stripes 36 of adhesive on the outer surface of the moisture barrier 28 extending along the longitudinal central axis of the shield for substantially the length of the shield. Any suitable positioning adhesive 36 can be used for the stripes, such as a pressure sensitive hot melt adhesive. One particularly suitable material for the positioning adhesive 36 is available from National Starch and Chemical of Bridgewater, N.J. under the trade designation #34-5598. In order to protect the adhesive stripes 36 from degradation or being soiled by debris, a single release strip 38 (e.g., a release paper) is releasably secured over them. The release strip 38 can be formed of any suitable adhesive protective, yet easy to release, material. One particularly suitable material for the adhesive release strip 38 is available from Tekkote of Leonia, N.J. under the trade designation #11636.

Figure 2:
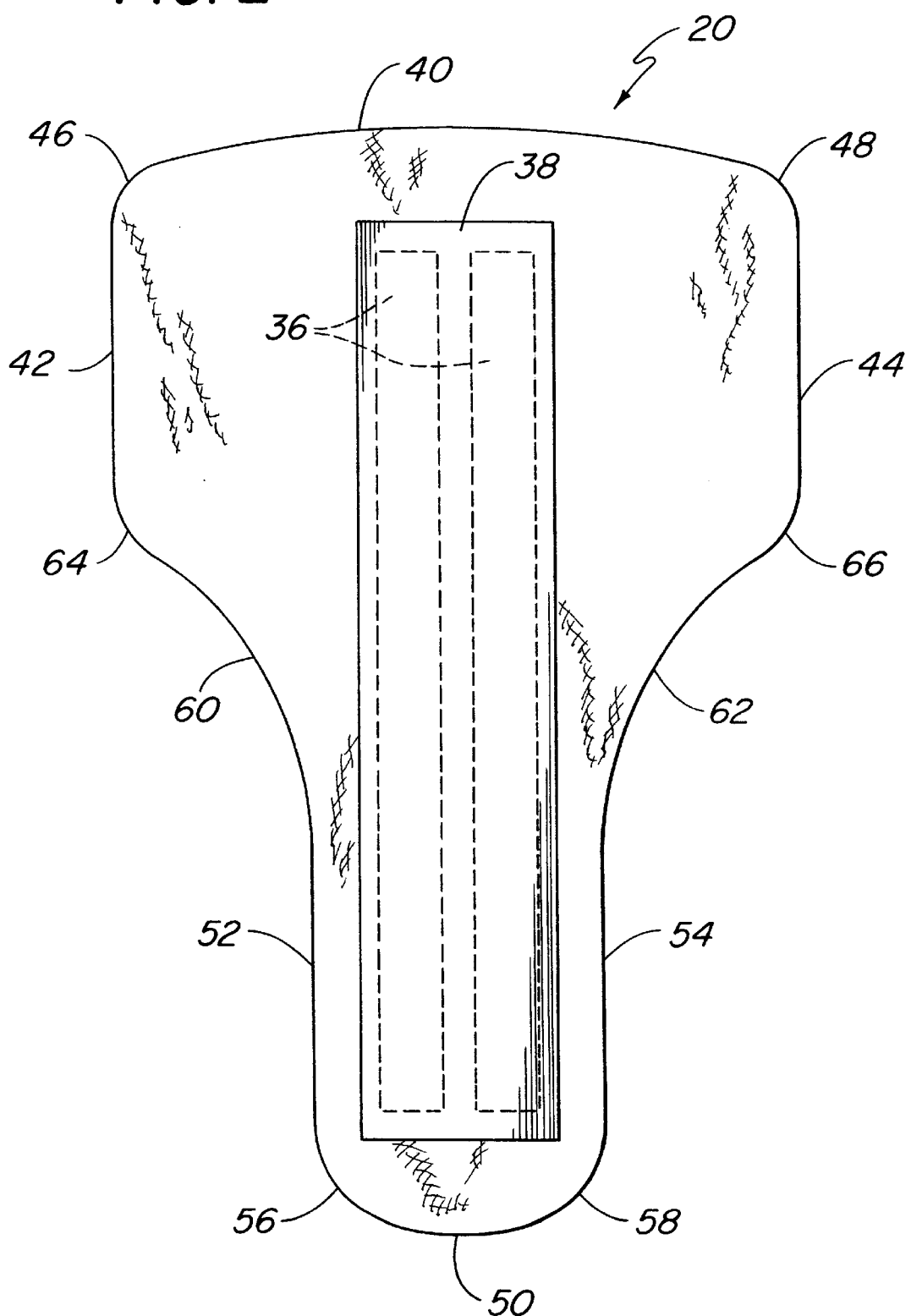
FIG. 2 is an enlarged plan view of the underside of the shield shown in FIG. 1.

As best seen in FIGS. 1 and 2, and as mentioned above, the chassis of the shield 20 is of a modified T-shape. To that end the upper or transverse portion 22 includes a top edge 40 which is a gentle convex arc extending between a pair of linear sides 42 and 44. The top edge 40 merges with the linear side 42 in a curved corner 46 and merges with the linear side 44 in another curved corner 48. The distance between the linear sides, i.e., the width of the upper portion 22, is approximately 152 mm. The lower or crotch portion 24 includes a bottom or rear edge 50 which is a convex arc extending between a pair of linear sides 52 and 54. The rear edge 50 merges with the linear side 52 in a curved corner 56 and merges with the linear side 54 in another curved corner 58. The distance between the linear sides 52 and 54, i.e., the width of the crotch portion 24, is approximately 64 mm. The linear side 52 of the crotch portion 24 merges with the linear side 42 of the upper transverse portion 22 in a gentle concave arcuate interface or edge 60. In a similar manner the linear side 54 of the crotch portion 24 merges with the linear side 44 of the upper transverse portion 22 in a gentle concave arcuate interface or edge 62. The radius of curvature of each of the arcuate edges 60 and 62 is sufficiently large to comfortably accommodate the inner surface of the thighs of the wearer. The arcuate edge 60 merges with the linear side 42 of the upper portion 22 in a curved corner 64, while the arcuate edge 62 merges with the linear side 44 of the upper transverse portion 22 in a curved corner 66. The distance between the crown of the top edge 40 and the crown of the bottom edge 50 measured along the central longitudinal axis of the shield is approximately 245 mm.

As should be appreciated by those skilled in the art from the foregoing, when the shield 20 is in place within the wearer's undergarment the front or upper portion 22 is disposed over the wearer's penis and lower abdomen region (thereby providing maximum coverage to prevent any leaking urine from contacting the wearer's undergarment), while the crotch portion 24 is located between the wearer's legs. Moreover, the gentle curved nature of the interface edges 62 and 64 between the upper portion and the crotch portion on each side of the shield ensures that there is good conformance with the inner surface of the wearer's thighs to prevent leakage of urine therefrom, while also rendering the shield comfortable and virtually invisible under the undergarment.

While the discussion heretofore has concentrated on the use of this shield on adult males, shields constructed in accordance with this invention can also be used by females, with or without slight modification, e.g., size changes, to accommodate the different anatomy involved. Thus, the use of gender related terms in this application is not to be limiting of the invention.

As should be appreciated from the foregoing the incontinent shield of the subject invention addresses the needs of the prior art for a concealable, comfortable, quiet, easy to conform to the wearer's body, shield to prevent the egress of small amount of urine. Moreover, the shield of this invention is a relatively low cost, easy to manufacture, compact article.

Without further elaboration the foregoing will so fully illustrate our invention that others may, by applying current or future knowledge, adopt the same for use under various conditions of service.

We claim:

1. A disposable absorbent shield arranged to be worn under clothing by a male person to trap and collect urine, said shield comprising a flexible chassis having an upper portion arranged to be located over the person's penis and contiguous lower abdominal region and a crotch portion arranged to be located over the person's crotch and between the person's legs, said chassis including a liquid absorbent core, an outer cover, and an inner liner, said liquid absorbent core being interposed between said outer cover and said inner liner, said chassis being a very thin, planar structure having a longitudinal central axis and a modified T-shaped periphery including an upper transverse portion forming said upper portion of said chassis and a downwardly extending longitudinal portion forming said crotch portion of said chassis, said upper portion having an upper edge and a lower edge, said crotch portion of said chassis having a pair of linear side edges extending parallel to said longitudinal central axis, one portion of said lower edge of said upper portion of said chassis merging with one of said side edges of said crotch portion in a first gently curved intermediate edge, said first intermediate edge being located on one side of said central longitudinal axis at the center of said longitudinal central axis and conforming in shape to one of the legs of the wearer, another portion of said lower edge of said upper portion of said chassis merging with the other of said side edges of said crotch portion in a second gently curved intermediate edge, said second intermediate edge being located at the center of said longitudinal central axis but on the opposite side of said central longitudinal axis as said first intermediate edge, said second intermediate edge conforming in shape to the other of the legs of the wearer, said chassis being arranged to be bent into a desired shape to conform to the body of the wearer.

2. The disposable absorbent shield of claim 1 wherein said outer cover is fluid impervious.

3. The disposable absorbent shield of claim 2 wherein said outer cover is formed of a polymeric film.

4. The disposable absorbent shield of claim 1 wherein said inner liner comprises a moisture pervious material.

5. The disposable absorbent shield of claim 4 wherein said moisture pervious material comprises a fibrous material or an apertured polymeric material.

6. The disposable absorbent shield of claim 1 wherein said core is formed of an air-laid composite material.

7. The disposable absorbent shield of claim 6 wherein said composite material additionally comprises a super absorbent polymer.

8. The disposable absorbent shield of claim 1 wherein said outer cover is formed of a polymeric film, said inner liner is formed of a fibrous material or an apertured polymeric material, and said core is formed of an air-laid composite material including a super absorbent polymer.

9. The disposable absorbent shield of claim 1 additionally comprising an adhesive located on said outer cover for mounting said absorbent shield in a garment.

10. The disposable absorbent shield of claim 9 additionally comprising a release strip releasably secured over said adhesive.

11. The disposable absorbent shield of claim 1 wherein said chassis is in the range of approximately 0.2 mm to 6 mm thick.

12. The disposable absorbent shield of claim 11 wherein said chassis is approximately 1.0 mm thick.

13. The disposable absorbent shield of claim 1 wherein said first and second gently curved intermediate edges each have a radius of curvature of approximately 76 mm.

14. The disposable absorbent shield of claim 13 wherein said chassis is in the range of approximately 0.2 mm to 6 mm thick.

15. The disposable absorbent shield of claim 14 wherein said chassis is approximately 1.0 mm thick.

16. The disposable absorbent shield of claim 1 wherein said upper transverse portion is approximately 152 mm wide, said downwardly extending longitudinal portion is approximately 254 mm long, and each of said first and second gently curved intermediate edges each have a radius of curvature of approximately 76 mm.

* * * * *